United States Patent [19]

VanMiddlesworth et al.

[11] Patent Number: 5,164,375
[45] Date of Patent: Nov. 17, 1992

[54] ANTIFUNGAL AGENT

[75] Inventors: Frank VanMiddlesworth, Fanwood; Kenneth E. Wilson, Westfield; Otto D. Hensens, Red Bank; Deborah Zink, Manalpan; Maria B. Lopez, Hillside, all of N.J.

[73] Assignee: Merck & Company, Inc., Rahway, N.J.

[21] Appl. No.: 766,311

[22] Filed: Sep. 27, 1991

[51] Int. Cl.$^5$ ............................................. A61K 31/70
[52] U.S. Cl. ........................................ 514/25; 514/75; 514/78; 536/117
[58] Field of Search .................. 536/117; 514/25, 75, 514/78

[56] References Cited

U.S. PATENT DOCUMENTS

| | | | |
|---|---|---|---|
| 4,624,919 | 11/1986 | Kokusho et al. | 536/117 |
| 4,912,094 | 3/1990 | Myers et al. | 536/117 |
| 4,914,197 | 4/1990 | Yamamoto et al. | 536/117 |
| 4,916,220 | 4/1990 | Galzigna et al. | 536/117 |
| 4,987,237 | 1/1991 | Myers et al. | 536/117 |

Primary Examiner—Thurman K. Page
Assistant Examiner—G. S. Kishore
Attorney, Agent, or Firm—Alice O. Robertson; Raymond M. Speer

[57] ABSTRACT

A phospholipid having the formula

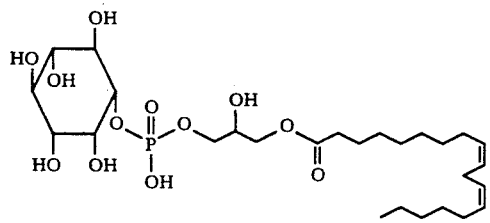

is described. The compound has antifungal properties.

2 Claims, No Drawings

ANTIFUNGAL AGENT

A phospholipid having the formula

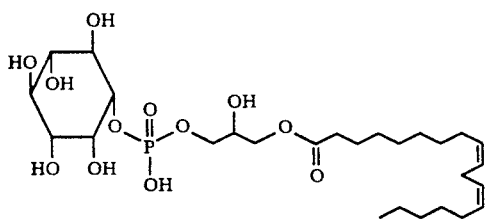

which had been isolated from a fermentation of *Aspergillus fumigatus* has been obtained by chemico-enzymatic synthesis. The compound has a broad spectrum of antifungal properties and is of very low mammalian toxicity.

The compound is a white solid highly soluble in water.

The compound has the following spectral properties which support the structure of the natural and the synthetic product.

Nuclear Magnetic Resonance Spectra $^1$H-NMR (300 MHz CD$_3$OD) δ0.92 (t, J=6 Hz, 3H), 1.28–1.42 (m, 14H), 1.56–1.68 (m, 2H), 2.07 (dd, J=7 and 6 Hz, 4H), 2.45 (t, J=8 Hz, 2H), 2.78 (t, J=6 Hz, 2H), 3.20 (t, J=9 Hz, 2H), 3.38 (dd, J=3 and 8 Hz, 1H), 3.62 (t, J=10 Hz, 1H), 3.77 (t, J=9 Hz, 1H), 3.92 (ddd, J=3, 7. and 10 Hz, 1H), 3.98 (dd, J=2 and 7 Hz, 2H), 4.06–4.12 (m, 1H), 4.15 (dd, J=4 and 8 Hz, 1H), 4.21 (t, J=3 Hz, 1H), 5.3–5.4 (m, 4H).

$^{13}$C-NMR (75 MHz CD$_3$OD) δ14.4, 23.6 26.0 26.5 28.2(2x), 30.2(2x), 30.3, 30.5 30.7, 32.7, 34.9, 66.3, 67.8 (d, J=5.8 Hz), 70.0 (d, J=7.7 Hz), 72.9, 73.1 (d, J=1.9 Hz), 73.3 (d, J=5.5 Hz), 74.1 76.3, 78.4 (d, J=6.1 Hz), 129.1(2x), 130.9(2x), 175.4 ppm.

Mass Spectrum

FAB-MS (negative ion) indicated MW of 596 (observed (M-H) at m/z 595).

The compound was originally obtained as a very minor product in the fermentation of *Aspergillus fumigatus*, ATCC 20857. However, the compound was present in extremely low titers and since effort to reproduce the production has not been successful, a method for producing it by chemico-enzymatic synthesis has been devised.

The starting material for the chemico-enzymatic synthesis is preferably soy bean phosphatidyl inositol which is a substance which has as major component 1-palmitoyl (or stearoyl)-2-linoleoyl-3-glycerophosphatidyl-D-myo-inositol (Compound A).

Compound A is treated under mild conditions of pH 6–7 and ambient temperature, with a commercially available lipase preferably from *Rhizopus arrhizus* whereupon the stearate (or palmitate) is stereo-selectively cleaved to form lyso-phosphatidyl inositol (Compound B). This ester when treated at pH 8.5 in the presence of 50 mM TAPS buffer [N-tris[hydroxymethyl]-methyl-3-aminopropanesulfonic acid hydrochloride buffer] undergoes intramolecular transacylation to the more sterically favorable primary position producing the desired Compound I (as salt) of the present invention. The reaction may be illustrated by the following flow-dragram,

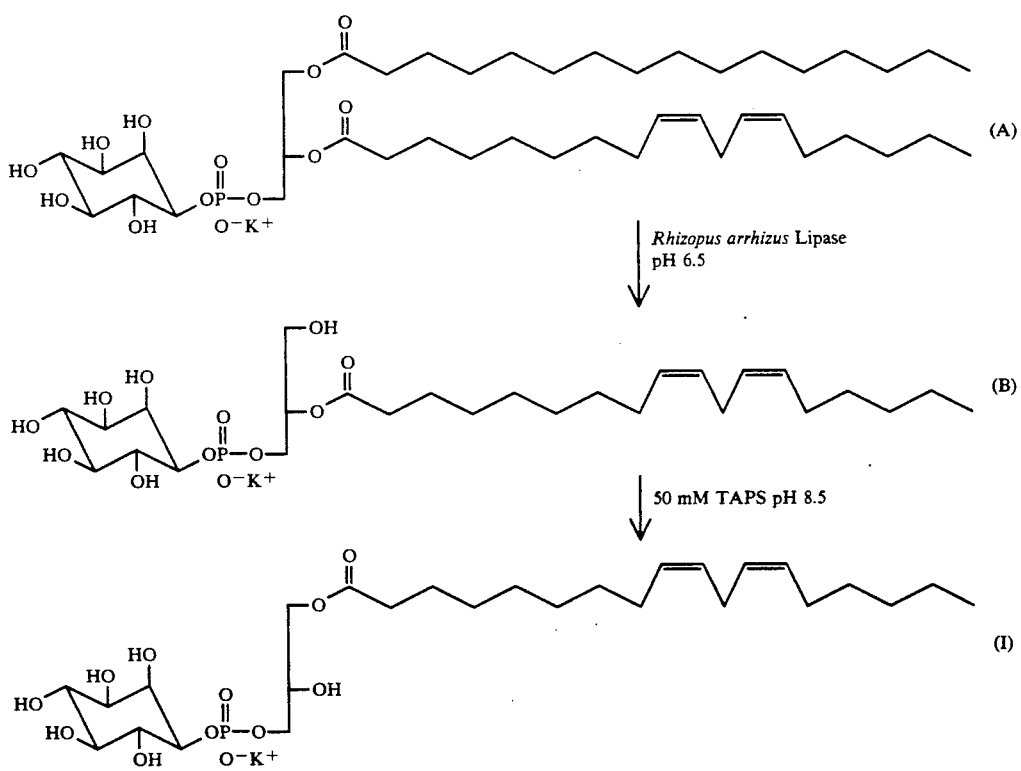

Compound I prepared by these steps exhibits identical physical properties as the natural product including thin layer chromatography (TLC), high performance liquid chromatography (HPLC), proton nuclear magnetic resonance ($^1$H-NMR), carbon nuclear magnetic resonance ($^{13}$C-NMR) and mass spectrum (MS negative ion FAB).

The compound has a broad spectrum of antifungal activity. The antifungal activity may be demonstrated in the following agar dilution assay.

In carrying out the assay, Compound I was solubilized in water and twofold dilutions were made with sterile distilled water to obtain final drug concentrations in the agar dilution assay plates ranging from 128 to 0.06 μg/ml.

The yeast cultures, maintained in yeast maltose (YM) broth, were transferred to fresh YM medium and incubated overnight at 35° C. with shaking (250 rpm). After incubation, each culture was diluted in sterile saline to yield a final concentration of $3 \times 10^5$ to $3 \times 10^6$ colony forming units (CFU/ml).

Each prepared plate was inoculated using a Denley Multipoint Inoculator (Denley, Sussex, England) which delivers approximately 0.001 milliliter to the agar surface resulting in inoculation of from $3 \times 10^2$ to $3 \times 10^3$ CFUs. The plates were incubated at 28° C. for 48 hours. The minimum inhibitory concentrations (MICs) were recorded as the lowest concentrations of drug showing no growth or less than three CFU/spot.

Useful antimycotic properties may be illustrated with the results demonstrating the superior effectiveness of Compound I against *Cryptococcus neoformans*, various Candida species and certain filamentous fungi as seen in the following table.

| Fungus | Strain No. | Minimum Inhibitory Concentration (mg/ml) |
|---|---|---|
| Cryptococcus neoformans | MY1051 | 16 |
| Cr. neoformans | MY1146 | 16 |
| Candida albicans | MY1058 | 64 |
| Ca. albicans | MY1055 | 32 |
| Ca. albicans | MY0992 | 32 |
| Ca. albicans | MY1013 | 64 |
| Ca. albicans | MY1029 | 32 |
| Ca. parapsilosis | MY1009 | 64 |
| Ca. parapsilosis | MY1010 | 32 |
| Ca. tropicalis | MY1011 | 32 |
| Ca. tropicalis | MY1012 | 16 |
| Ca. pseudotropicalis | MY1040 | 8 |
| Ca. krusei | MY1020 | 16 |
| Ca. rugosa | MY1022 | 16 |
| Ca. stellatoidea | MY1017 | 32 |
| Torulopsis glabrata | MY1059 | 32 |
| Sac. cerevisiae | MY1027 | 16 |
| Penicillium italicum | MF2819 | 64 |

The outstanding properties are most effectively utilized when the compound is formulated into novel pharmaceutical compositions with a pharmaceutically acceptable carrier according to conventional pharmaceutical compounding techniques.

The novel compositions contain at least a therapeutic amount of the active compound. Generally, the composition contains at least 1 percent by weight of Compound I. Concentrate compositions suitable for dilutions prior to use may contain 90 percent or more by weight. The compositions include compositions suitable for oral, topical, parenteral (including subcutaneous, intramuscular, and intravenous), pulmonary (nasal or buccal inhalation), other nasal and suppository administration, or insufflation. The compositions may be prepacked by intimately mixing Compound I with the components suitable for the medium desired.

When oral administration is to be employed, it may be with a liquid composition or a solid composition. For liquid preparations, the therapeutic agent is formulated with liquid carriers such as water, glycols, oils, alcohols, and the like, and for solid preparations such as capsules and tablets, solid carriers such as starches, sugars, kaolin, ethyl cellulose phosphate kaolin, talc, lactose, generally with lubricant such as calcium stearate, together with binders disintegrating agents and the like. Because of their ease in administration, tablets and capsules represent the most advantageous oral dosage form.

When administration is to be by injection, it may be presented in ampoules or in multidose containers, if necessary with an added preservative. The compositions may also take such forms as suspensions, solutions or emulsions in oily or aqueous vehicles such as 0.85 percent sodium chloride or 5 percent dextrose in water, and may contain formulating agents such as suspending, stablizing and/or dispersing agents. Buffering agents as well as additives such as saline or glucose may be added to make the solutions isotonic. The drug also may be solubilized in alcohol/propylene glycol or polyethylene glycol for drip intravenous administration. Alternatively, the active ingredients may be in powder form for reconstituting with a suitable vehicle prior to administration.

When administration is to be by inhalation, the compound is conveniently delivered in the form of an aerosol spray presentation from pressurized packs of nebulizers. The preferred delivery system for inhalation is a metered dose inhalation (MDI) aerosol, which may be formulated as a suspension or solution of Compound I in suitable propellants, such as fluorocarbons or hydrocarbons.

It is especially advantageous to formulate the compositions in unit dosage form (as hereinafter defined) for ease of administration and uniformity of dosage. The term "unit dosage form" refers to physically discrete units, each unit containing a predetermined quantity of active ingredient which singly or in multiples would produce the desired therapeutic effect in association with the pharmaceutical carrier. Examples of such unit dosage forms are tablets, capsules, pills, powder packets, wafers, measured units in ampoules or in multidose containers and the like. A unit dosage of the present invention will generally contain from 100 to 200 milligrams of Compound I. Compositions in unit dosage form constitutes an aspect of the present invention.

The following examples illustrate the invention but are not to be construed as limiting

EXAMPLE I

Synthesis of Compound I

A 4 milliliter aqueous suspension consisting of 12 mg. deoxycholate, 18 mg bovine serum albumin, 5 mM calcium sulfate and 100 mM of pH 6.5 borate buffer was added with sonication and stirring to 40 milligrams (0.049 mmol) of a dried sample of soy bean phosphatidyl inositol. *Rhizopus arrhizus* lipase (one million units) was then added and the reaction was stirred at room temperature. After two hours, the reaction was quenched by the addition of 4 milliliters of 50 percent methanol. The resulting solution was loaded onto an open reverse phase (RP) C-18 column (5 milliliters of Baker octadecyl, 40 micron) and eluted with a methanol/water gradient to obtain from the 70–75 percent methanol fractions crude lyso-phosphatidyl inositol (Compound B).

The crude lyso-phosphatidyl inositol was dissolved in 2.5 milliliters of 50 mM TAPS hydorchloride buffer (pH 8.5) with stirring at room temperature. The reaction was monitored by HPLC (Dupont "ZORBAX" ODS 25 cm, UV at 205 nm, 67/33 10 mM potassium phosphate (pH 6.5)/acetonitrile, 1 ml/min, retention times 11.2 min for Compound B and 14.2 min for Compound I). After 18 hours, the reaction was applied to an open RPC-18 column (as above) and eluted with a methanol/water gradient to obtain from 80 percent methanol, 15 milligrams of Compound I which on lyophilization from water was a white solid. This compound had the spectral properties above detailed.

EXAMPLE II

Isolation of Compound from Fermentation Broth of *Aspergillus fumigatus* MF 5038

A pilot plant fermentation broth from fermentation of *Aspergillus fumigatus* MF 5038 (as hereinafter described), which then had been put through a "DIAION" SP-20 column (styrene-divinylbenzene copolymer, Mitsubishi Chemical Industries) and concentrated to about 2 liters, was received and served as starting material for the isolation. The isolation process for Compound I was followed by standard agar disc diffusion assay techniques using *Candida pseudotropicalis* MY 1100 as assay organism.

The 2-liter sample of concentrated SP 207 eluate was further concentrated under reduced pressure to a volume of about 1 liter and then extracted twice with ethyl acetate. The aqueous layer remaining was concentrated to dryness after about 5 milliliters of 2 octanol had been added to inhibit foaming and 500 milliliters of methanol was added to the residue, the resulting mixture stirred for two hours, and then filtered through a sintered glass funnel.

The filtrate was chromatographed on a "SEPHADEX" (Pharmacia) LH-20 column (6 cm ID × 130 cm) with methanol. Seven runs were made, after which the seven rich cuts were combined, concentrated and filtered through a sintered glass funnel. The filtrate (125 ml) was diluted with 67 ml of water and applied to a 2.2 L column (7 cm ID × 57 cm) of E. Merck LiChroprep RP18 resin (25–40 micron), equilibrated in 65/35 methanol-water. The column was washed with 8 L of 65/35 methanol-water and eluted stepwise with 70/30 methanol-water (Fractions 1–8, 500 ml each) and 75/25 methanol-water (Fractions 9–39, 250 ml each). Fractions 5 and 6 were combined and concentrated to dryness to obtain 39 mg of Compound I as a white solid.

The solid was found to have a broad spectrum of antifungal activity and low toxicity.

The isolate had the following nuclear magnetic resonance properties.

$^1$H-NMR (400 MHz CD$_3$OD) δ0.90 (t, J=7 Hz, 3H), 1.28–1.42 (m, 14H), ∼1.61 (m, 2H), 2.06 m, 4H), 2.35 (t, J=7.5 Hz, 2H), 2.77 (t, J=6.5 Hz, 2H) 3.19 (t, J=9.5 Hz, 1H), 3.37 (dd, J=3 and 10 Hz, 1H), 3.62 (t, J=9.5 Hz, 1H), 3.97 (m, 2H), 4.05–4.13 (m, 1H), 4.17 (m, 1H), 4.21 (t, J=3 Hz, 1H), 5.3–5.4 (m, 4H).

$^{13}$C-NMR (100 MHz CD3OD) δ14.5, 23.7, 26.0 26.6 28.2(2x), 30.3(2x), 30.4, 30.5, 30.8, 32.7, 34.9, 66.2, 67.8 (d, J=5 Hz), 69.9 (d, J=8 Hz), 72.8, 73.0 (d, J=3 Hz), 73.2 (d, J=5.5 Hz), 74.0 76.3, 78.4 (d, J=6 Hz) 128.88, 128.90, 130.69, 130.74, 175 ppm.

Fermentation Producing the Isolated Metabolite

Frozen vials of *Aspergillus fumigatus* MF 5038 (properties hereinafter described) were inoculated in 54 milliliters of KF medium of the following composition per liter: corn steep liquor, 5 g; tomato paste, 40 g; oat flour, 10 g; glucose monohydrate, 10 g; FeSO$_4$·7H$_2$O, 10 mg; MnSO$_4$·H$_2$O, 10 mg; CuCl$_2$·2H$_2$O, 0.25 mg; CaCl$_2$·2H$_2$O, 1 mg; H$_3$BO$_3$, 0.56 mg; (NH$_4$)$_6$Mo$_7$O$_{24}$·4H$_2$O, 0.19 mg; ZnSO$_4$·7H$_2$O, 2 mg and incubated at 27° C. for two days at 220 rpm. Twenty milliliter samples were then used to inoculate four 2 liter flasks containing 500 milliliters of KF medium and the inoculated medium was incubated at 25° C. for two days at 220 rpm. The contents of the flasks were then used to inoculate two 300 liter seed fermenters containing 180 liters of KF medium and 1 milliliter per liter of propylene glycol to reduce foaming. The seed fermenters were operated at 27° C., air flow of 100 liters/min, pressure of 0.5 kg/cm$^2$ gauge and an agitator speed of 150 rpm to provide seed media.

The two seed media (75 liters each) were used to inoculate two production fermenters containing 750 liter of production media, each medium of the following composition per liter: glucose monohydrate, 10 g; "ARDAMINE" PH, 5 g; glycerol, 10 g; ammonium sulfate, 2 g; soybean meal, 5 g; tomato paste, 5 g; sodium citrate, 2 g. and the resulting media cultivated without agitation or back pressure at 25° C. and air-flow of 10 liters per minutes for 14 days.

Fermentation broth was added to an equal volume of methanol and filtered to remove solids. The filtrate which contained the product was partially concentrated under vacuum and then the concentrate was loaded onto a column containing adsorbent resin (Dianon HP-20; Mitsubishi Chemical Co.). The column was washed with 60 and 80 percent aqueous methanol and the product was eluted with 100 percent methanol. The methanol fractions containing the product were partially concentrated under vacuum and the water content of the concentrate was adjusted to 60% by addition of water. The feed was loaded onto a column containing adsorbent resin (SEPABEADS SP-207; Mitsubishi Industries), the column was washed with 50 percent aqueous methanol and the product was eluted with 100 percent methanol. Methanol fractions containing the product were partially concentrated under vacuum for further processing land isolation of metabolite.

The *Aspergillus fumigatus* MF 5038 which was used in this isolation is one which has been deposited at the American Type Culture Collection and was given ATCC number 20857.

The morphological and cultural characteristics of MF 5038 ATCC 20857 are as follows:

A. Morphological Characteristics

1. Condidial heads erect, compact and columnar, olive-green in color, darkening with age.
2. Vesicles are flask-shaped, smooth, dark olive-green in color, especially in upper part.
3. Sterigmata are in one series, also pigmented and present mostly on upper half.
4. Conidia are globose, echinulate to roughened, dark olive-green in mass, 2.3–3.0 microns in diameter.
5. No perithecia or sclerotia were observed.

B. Cultural characteristics

1. Potato dextrose agar. Colonies are white at first, becoming green as conidia develop and becoming dark green to almost black as colonies age. Colonies are rapid growing, spreading and become flocculent. Reverse is yellowish brown, darkening as culture ages. Conidial structures more abundant than on Czapek Dox or Sabouraud maltose agars. Growth is good at 28° C. and 37° C., very poor at 42° C.

2. Czapek-Dox agar. Colonies are spreading, velvety, cream-colored with brownish areas. Reverse is yellowish brown. Conidial structures very few.

3. Sabouraud maltose agar. Colonies are spreading, velvety, white becoming cream-colored with light brown areas. Reverse is yellowish brown. Conidial structures very few.

What is claimed is:

1. A compound having the formula

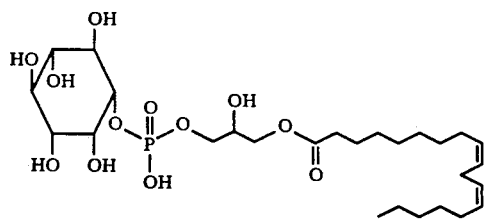

or an alkali metal salt thereof.

2. An antifungal composition comprising an effective antifungal amount of the compound of claim 1, in a suitable pharmaceutical carrier.

* * * * *